United States Patent
Koehler

(10) Patent No.: US 10,437,132 B1
(45) Date of Patent: Oct. 8, 2019

(54) METHODS AND APPARATUS FOR ACOUSTO-OPTIC NON-UNIFORMITY CORRECTION AND COUNTER-COUNTERMEASURE MECHANISMS

(71) Applicant: RAYTHEON COMPANY, Waltham, MA (US)

(72) Inventor: Elka E. Koehler, Tucson, AZ (US)

(73) Assignee: RAYTHEON COMPANY, Waltham, MA (US)

( * ) Notice: Subject to any disclaimer, the term of this patent is extended or adjusted under 35 U.S.C. 154(b) by 59 days.

(21) Appl. No.: 15/926,229

(22) Filed: Mar. 20, 2018

(51) Int. Cl.
| | |
|---|---|
| *G02F 1/33* | (2006.01) |
| *G02F 1/11* | (2006.01) |
| *G01N 21/47* | (2006.01) |
| *G02F 1/225* | (2006.01) |

(52) U.S. Cl.
CPC .......... *G02F 1/332* (2013.01); *G01N 21/4795* (2013.01); *G02F 1/11* (2013.01); *G02F 1/2255* (2013.01)

(58) Field of Classification Search
CPC .......... G02F 1/332; G02F 1/11; G02F 1/2255; G01N 21/4795
USPC ...................................... 359/285–305; 385/7
See application file for complete search history.

(56) References Cited

U.S. PATENT DOCUMENTS

| | | |
|---|---|---|
| 2015/0358557 A1 | 12/2015 | Terre et al. |
| 2017/0115160 A1 | 4/2017 | Fest |

FOREIGN PATENT DOCUMENTS

| | | |
|---|---|---|
| EP | 0647064 A1 | 4/1995 |
| GB | 2437395 A | 10/2007 |
| JP | H02206976 A | 8/1990 |
| WO | 9847102 A2 | 10/1998 |

OTHER PUBLICATIONS

International Search Report and Written Opinoin in application No. PCT/US2018/065142 dated May 10, 2019.

*Primary Examiner* — Mahidere S Sahle
(74) *Attorney, Agent, or Firm* — Lando & Anastasi, LLP

(57) ABSTRACT

Examples provide a compact, dynamic non-uniformity correction mechanism and counter-countermeasure mechanism. In one example an optical imaging system includes an imaging sensor configured to receive optical radiation and to produce an image of a viewed scene from the optical radiation, an optical train including at least one optical component configured to receive the optical radiation from the viewed scene and to focus the optical radiation to the imaging sensor, and an acousto-optic modulator positioned in the optical train and having an ON state and an OFF state, the acousto-optic modulator being configured in the OFF state to pass the optical radiation, and the acousto-optic modulator being configured in the ON state to diffract the optical radiation and blur the image produced by the imaging sensor from the diffracted optical radiation.

20 Claims, 5 Drawing Sheets

METHODS AND APPARATUS FOR ACOUSTO-OPTIC NON-UNIFORMITY CORRECTION AND COUNTER-COUNTERMEASURE MECHANISMS

FEDERALLY SPONSORED RESEARCH

This invention was made with government support under Grant No. FA8651-16-D-0314-0002 awarded by the Department of Defense. The U.S. government has certain rights in this invention.

BACKGROUND

A wide variety of optical systems include an imaging sensor that typically includes an array of photo-sensitive detectors, often termed a focal plane array (FPA). Each detector produces an output that corresponds to a pixel in the image produced by the imaging sensor. Each detector generally includes a photo-diode and electronic components for measuring the intensity of received light. An array may include many hundreds or thousands of detectors. Each detector in the array may have a slightly different sensitivity or response to same received light (i.e., light with the same wavelength, intensity, etc.). This non-uniform sensitivity yields Fixed Pattern Noise (FPN) in the images produced by the detector array. The fixed pattern noise causes some pixels in the image to be too bright, while others are too dark. This negatively impacts the Signal to Noise Ratio (SNR) of the imaging sensor, and the guidance system of a seeker when the imaging sensor is used to guide a projectile to its intended target. Therefore, to be able to produce accurate, high resolution images and accurately track a target in a seeker, it can be important to compensate for the non-uniformity in the detector outputs across the array.

A Non-Uniformity Compensation (NUC) system adjusts each pixel gain and offset to compensate for the FPN by applying a unique correction to each pixel. Typically a Two Point Non-Uniformity Compensation (Two Point NUC) is done on the ground prior to flight to make the corrections at two specific scene temperatures. However, if during flight the sensor is exposed to background scenes that are far from the corrected temperatures, the system noise will rise in proportion to the background noise. Therefore, in situ, real time, scene based NUC correction during flight may be necessary. An Adaptive Non-Uniformity Compensation (ADNUC) system adjusts each pixel dynamically to compensate for the differing sensitivity of each detector in the FPA.

Non-uniformity correction can be done by masking the array during a calibration procedure, such that every detector has the same, known input, and measuring the output from each detector. Differences in the outputs can be used to provide gain and offset calibration coefficients that are applied, for example, by altering the bias voltages at each detector, or during image processing, such that for the same known input to every detector, every pixel in the image has the same color and intensity. Conventionally, masking the array is done by placing a light-blocking shield over the array to prevent the detectors from receiving light, and the outputs are measured in this "dark state."

Non-uniformity correction is often needed in optical systems that operate in the visible spectrum (e.g., imaging systems that produce color images of a viewed scene) or the infrared spectrum (e.g., seekers or other thermal imaging systems). In seekers, non-uniformity correction is typically done using an opaque (light-blocking) paddle that is driven by a mechanical servo to move the paddle into and out of the optical path or field-of-view of the imaging sensor. However, the need to move the paddle into and out of the field-of-view of the sensor requires bulky moving parts, and this type of mechanism can be difficult to incorporate into systems with constrained packaging requirements.

SUMMARY OF INVENTION

Aspects and embodiments are directed to a compact, dynamic non-uniformity correction mechanism and counter-countermeasure mechanism.

According to one embodiment, an optical imaging system comprises an imaging sensor configured to receive optical radiation and to produce an image of a viewed scene from the optical radiation, an optical train including at least one optical component configured to receive the optical radiation from the viewed scene and to focus the optical radiation to the imaging sensor, and an acousto-optic modulator positioned in the optical train and having an ON state and an OFF state, the acousto-optic modulator being configured in the OFF state to pass the optical radiation, and the acousto-optic modulator being configured in the ON state to diffract the optical radiation and blur the image produced by the imaging sensor from the diffracted optical radiation.

In one example the acousto-optic modulator includes an acousto-optic material configured to support an acoustic wave, a piezo-electric transducer coupled to the acousto-optic material and configured to generate the acoustic wave in the acousto-optic material in response to an RF signal applied to the piezo-electric transducer, and an acoustic absorber coupled to the acousto-optic material. The acousto-optic material may be sandwiched between the piezo-electric transducer and the acoustic absorber. In one example the acousto-optic material is Germanium. In other examples other acousto-optic materials can be used. For example, the acousto-optic material may be any one of Lithium Niobate, Gallium Phosphide, a chalcogenide glass, fused Silica, quartz, and Tellurium Oxide. In one example the optical train includes a window, and the acousto-optic modulator is integrated with the window. The optical radiation can be infrared radiation, for example. In one example the optical imaging system is a seeker.

The optical imaging system may further comprise a controller coupled to the acousto-optic modulator, the controller being configured to dynamically switch the acousto-optic modulator between the ON state and the OFF state. In one example the optical imaging system further comprises a photosensor coupled to the controller, the photosensor configured to receive a laser beam from the viewed scene and to produce a signal in response to receiving the laser beam, and the controller being further configured to receive the signal from the photosensor and to switch the acousto-optic modulator into the ON state in response to receiving the signal from the photosensor. In one example the controller is configured to produce non-uniformity calibration coefficients based on outputs from the imaging sensor when the acousto-optic modulator is in the OFF state, and to adjust the image produced by the imaging sensor from the optical radiation when the acousto-optic modulator is in the OFF state to remove fixed pattern noise from the image.

According to another embodiment an infrared seeker system comprises an imaging sensor sensitive to infrared radiation and configured to receive the infrared radiation from a viewed scene and to produce an image from the infrared radiation, an optical train including at least one optical component configured to receive the infrared radiation from the viewed scene and to focus the infrared radiation to the imaging sensor, and an acousto-optic modulator positioned in the optical train and having an ON state and an OFF state, the acousto-optic modulator being transparent to the infrared radiation in the OFF state, and the acousto-optic modulator being configured in the ON state to diffract the infrared radiation and blur the image produced by the imaging sensor from the diffracted infrared radiation.

In one example the acousto-optic modulator includes an acousto-optic material configured to support an acoustic wave, a piezo-electric transducer coupled to the acousto-optic material and configured to generate the acoustic wave in the acousto-optic material in response to an RF signal applied to the piezo-electric transducer, and an acoustic absorber coupled to the acousto-optic material. In one example the acousto-optic material is Germanium. In other examples other acousto-optic materials can be used. In one example the at least one optical component includes at least one lens, and the optical train further includes a filter and a window, the filter and the at least one lens being positioned between the window and the imaging sensor, and wherein the acousto-optic modulator is integrated with the window. The filter may be configured to pass the infrared radiation in a spectral band of interest including the mid-wave infrared spectral band and the long-wave infrared spectral band and to block optical radiation outside the spectral band of interest.

In one example the infrared seeker system further comprises a controller coupled to the acousto-optic modulator, the controller being configured to dynamically switch the acousto-optic modulator between the ON state and the OFF state. The infrared seeker system may further comprise a photosensor coupled to the controller, the photosensor configured to receive a direct or indirect laser beam from the viewed scene and to produce a signal in response to receiving the laser beam, the controller being further configured to receive the signal from the photosensor and to switch the acousto-optic modulator into the ON state in response to receiving the signal from the photosensor. In one example the controller is configured to produce non-uniformity calibration coefficients based on outputs from the imaging sensor when the acousto-optic modulator is in the OFF state, and to adjust the image produced by the imaging sensor from the infrared radiation when the acousto-optic modulator is in the OFF state to remove fixed pattern noise from the image.

Another embodiment is directed to an optical imaging system with counter-countermeasure capability. The optical imaging system may comprise an imaging sensor configured to receive optical radiation and to produce an image of a viewed scene from the optical radiation, an optical train including at least one optical component configured to receive the optical radiation from the viewed scene and to focus the optical radiation to the imaging sensor, an acousto-optic modulator positioned in the optical train and having an ON state and an OFF state, the acousto-optic modulator being configured in the OFF state to pass the optical radiation, and the acousto-optic modulator being configured in the ON state to diffract the optical radiation and blur the image produced by the imaging sensor from the diffracted optical radiation, a controller coupled to the acousto-optic modulator, the controller being configured to dynamically switch the acousto-optic modulator between the ON state and the OFF state, and a photosensor coupled to the controller, the photosensor configured to receive a laser beam from the viewed scene and to produce a signal in response to receiving the laser beam, the controller being further configured to receive the signal from the photosensor and to switch the acousto-optic modulator into the ON state in response to receiving the signal from the photosensor.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures.

DETAILED DESCRIPTION

As discussed above, typical non-uniformity correction (NUC) in seekers is done with a mechanical servo-driven paddle that is moved into and out of the field-of-view of the sensor. This approach can be difficult to implement due to space constraints and adds significant complexity to the system. Aspects and embodiments provide purely electronically driven solid state NUC method that may be simpler, less expensive, more robust, and allow implementation on a wider variety of systems with space constraints than conventional NUC methods. In addition, aspects and embodiments provide a counter-countermeasure (CCM) mechanism for use in seekers or other optical systems.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Figure 1:
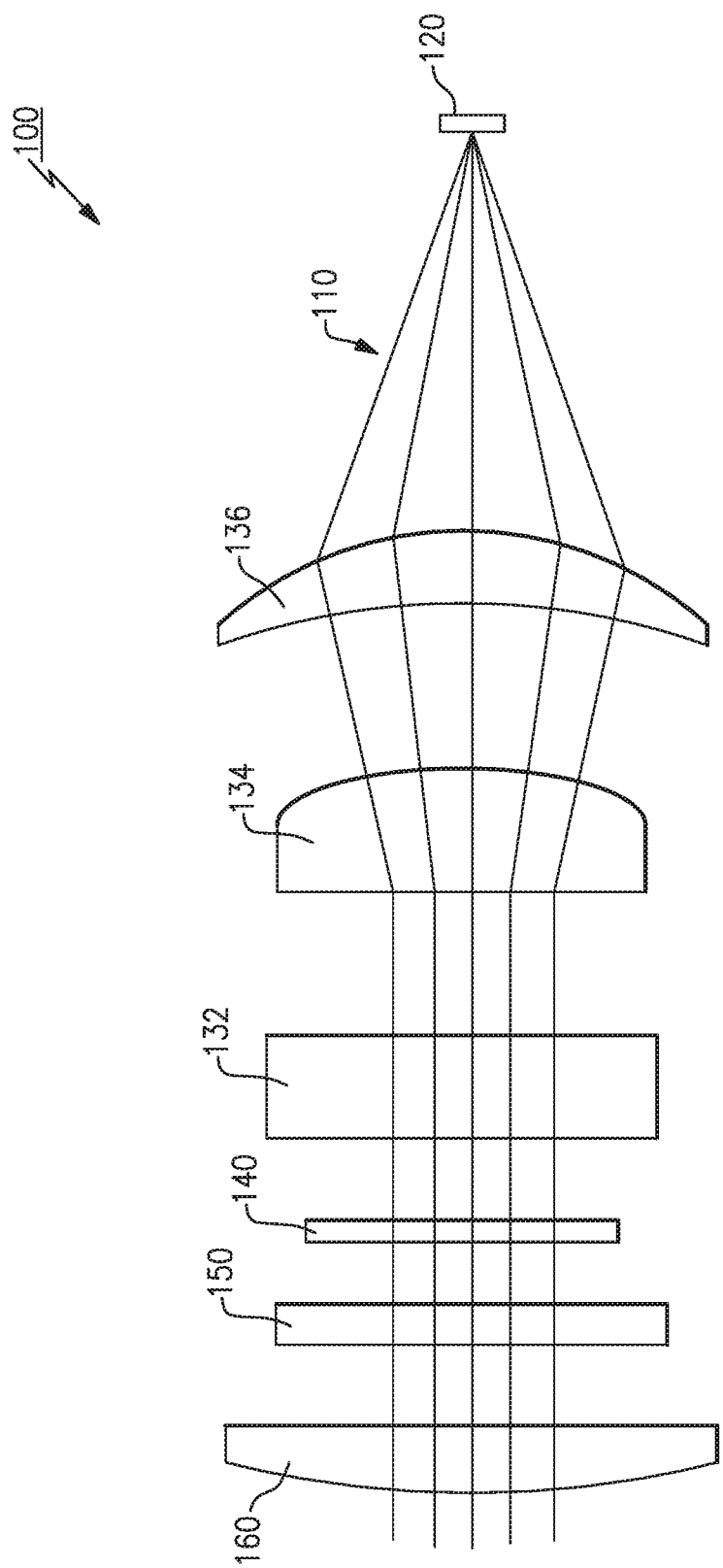
FIG. 1 is a diagram of one example of an optical system according to aspects of the present invention.

FIG. 1 illustrates an example of an optical system, such as a seeker, for example, in which the NUC or CCM mechanisms and methods of various embodiments may be implemented. The optical system 100 includes a plurality of optical elements that direct and focus incident optical radiation 110 onto an imaging sensor 120. As used herein, the term optical radiation refers to non-ionizing electromagnetic radiation in the one or more optical regions of the electromagnetic spectrum, including the visible, infrared, or ultraviolet spectral bands, that can be manipulated (e.g., reflected, refracted, focused, etc.) by conventional optical elements, such as mirrors or lenses. The imaging sensor 120 can include any type of optical detector that receives the incident optical radiation 110 and produces an electrical output signal indicative of at least one property of the received optical radiation (such as, but not limited to, intensity or color). In one example, the imaging sensor 120 is a multi-pixel focal plane array sensor. In the example illustrated in FIG. 1, the optical elements that direct and focus the optical radiation 110 onto the detector 120 include three lenses, 132, 134, and 136; however, in other examples any combination of lenses, mirrors, or both can be used. The optical system 100 may also include a filter 140 configured to spectrally filter the incident optical radiation 110. In one example the filter 140 can be configured to limit the spectral range of the optical radiation reaching the imaging sensor 120 to one or more spectral bands of interest.

In certain applications, such as seekers, where the imaging sensor 120 is operating in the thermal infrared spectral region, the sensor and at least some of the optical elements can be housed within a cooled chamber (not shown), such as a Dewar, for example, to reduce thermal noise. This cooled chamber includes a window that is optically transparent to infrared optical radiation to allow the incident optical radiation to enter the cooled chamber and reach the imaging sensor 120. In other applications, even of cooling (also referred to as "cold shielding") is not required, the detector and optionally other components can be housed within a protective chamber that also includes an optically transparent window. Accordingly, as shown in FIG. 1, in certain embodiments the optical system 100 includes a window 150 that is optically transparent in at least one spectral band of interest.

Certain seekers used in tactical missiles, for example, are packaged within the nose cone of the missile. Accordingly, in certain examples, the optical system 100 can include a dome 160 positioned in front of (i.e., towards the viewed scene) of the window 150. In other applications, the dome 160 may represent any outer packaging of the optical system 100, not limited to a component of a missile or other flight projectile.

The optical radiation 110 from a viewed scene passes through the dome 160, through the window 150, is filtered by the filter 140, and directed and focused by the lenses 132, 134, 136 onto the imaging sensor 120. As discussed above, the optical radiation 110 may include infrared wavebands or visible light. According to one embodiment, the imaging sensor 120 includes an array of n×m infrared detectors, n and m being integer numbers. Each detector has slightly different sensitivity to infrared radiation. As discussed above, this non-uniform sensitivity causes sensor fixed pattern noise, which is manifested in the image by some pixels being too dark and some being too bright.

Figure 2:
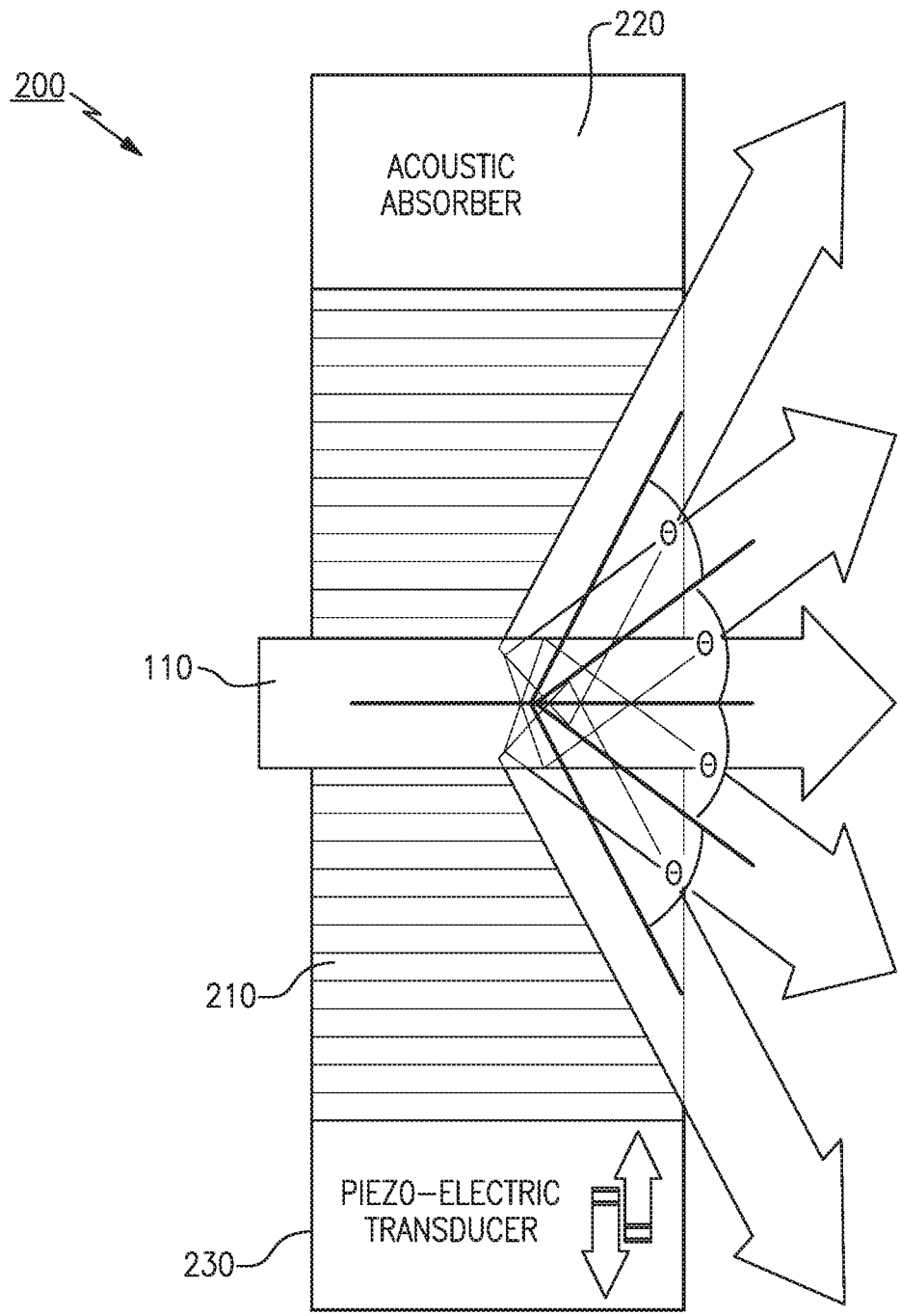
FIG. 2 is a block diagram of one example of an acousto-optic modulator as may be used in the optical system of FIG. 1 according to aspects of the present invention.
Figure 3:
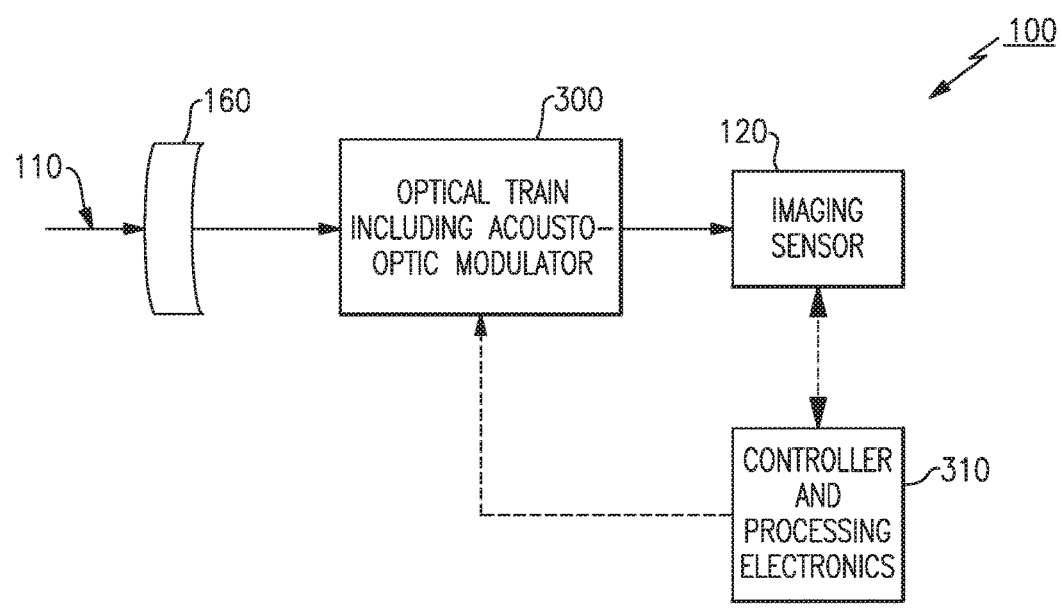
FIG. 3 is a block diagram of an example of an optical system incorporating an acousto-optic modulator according to aspects of the present invention.

According to one embodiment, an acousto-optic modulator is used to provide non-uniformity correction in the optical system 100. An example of an acousto-optic modulator 200 is illustrated in FIG. 2. As shown in FIG. 3, the acousto-optic modulator 200 can be positioned in the optical system 100 between the dome 160 and the imaging sensor 120, and receives the optical radiation 110. In one example the acousto-optic modulator 200 can be implemented in the window 150, as discussed further below; however, in other examples the acousto-optic modulator can be positioned anywhere along the optical train 300 on the scene or object-space side of the imaging sensor 120 to receive the incident optical radiation 110 before it reaches the imaging sensor 120. The acousto-optic modulator 200 has an ON state in which it acts on the optical radiation 110, as discussed below, and an OFF state in which it is substantially transparent to the optical radiation, allowing the optical radiation to pass through and reach the imaging sensor 120.

Referring to FIG. 2, the acousto-optic modulator 200 includes an acousto-optic material 210, an acoustic absorber 220, and a piezoelectric transducer 230. In the illustrated example, the acousto-optic material 210 is positioned between the acoustic absorber 220 and the piezoelectric transducer 230. The piezo-electric transducer can be bonded to the acousto-optic material 210. When an RF signal is applied to the piezo-electric transducer 230, a sinusoidal diffraction grating is generated from the acoustic wave in the acousto-optic material 210, and each wavelength of the incident light 110 spreads out over multiple diffraction orders, as shown in FIG. 2. By varying the acoustic frequency applied to the acousto-optic material 210 via the piezo-electric transducer 230, a range of varying grating periods can be generated. Thus diffracted light from a single grating produced with a unique RF frequency for a wideband radiation smears or blurs the image. Alternatively, the diffracted light can be swept across the detectors of the imaging sensor 120 by varying the RF frequency, resulting in a blurred image. This blurred image can provide a neutral background that can be used to calibrate the imaging sensor 120 and provide non-uniformity correction. For example, when an RF signal is applied to the acousto-optic modulator 200 to turn the acousto-optic modulator ON and provide the blurred image, the output of each detector (intensity or irradiance measurement) ideally should be the same. However, as discussed above, in reality there will be differences in the outputs from each detector. These differences can be recorded by a controller and processing electronics 310 coupled to the imaging sensor 120 and used to provide non-uniformity calibration coefficients to adjust the real images produced by the imaging sensor 120 when the acousto-optic modulator 200 is OFF to remove the fixed pattern noise and compensate for the differing sensitivity of each detector in the array. Scene-based non-uniformity correction compensates for non-uniformities caused by changes in the background of the imaging sensor 120 during flight of a seeker, for example.

The acousto-optic material 210 can be any of a variety of materials capable of responding to the piezo-electric transducer 230 to support an acoustic wave and also having suitable optical properties for use in the optical system 100. For example, when the acousto-optic modulator 200 is OFF, the acousto-optic material 210 should be highly transparent to the optical radiation 110 so as not to degrade the imaging performance of the optical system 100. Examples of acousto-optic materials 210 that can be used in embodiments of the acousto-optic modulator 210 include Germanium (for mid-wave and long-wave infrared applications), Lithium Niobate (for mid-wave infrared applications), Gallium Phosphide (for mid-wave and long-wave infrared applications), a chalcogenide glass, such as AMTIR (amorphous material transmitting infrared radiation; for mid-wave infrared applications), fused Silica (for mid-wave infrared applications), quartz (for mid-wave infrared applications), or Tellurium Oxide (for mid-wave infrared applications).

In certain embodiments and applications, particularly in infrared seekers, the window 150 is made of Germanium, and therefore, the window 150 can be adapted to also function as the acousto-optic modulator. Germanium is a suitable acousto-optic (AO) material 210 with a relatively high figure of merit, and can be used in both mid-wave and long-wave infrared applications. Thus, advantageously, optical systems using a Germanium window can be easily configured to include the acousto-optic modulator 200 without requiring significant modifications to the optical train 300 or arrangement or packaging of the optical components.

The controller 310 can be coupled to the acousto-optic modulator 200 and configured to control application of the RF signal (e.g., when the RF signal is applied and the frequency of the applied RF signal) to the piezo-electric transducer 230 to produce the blurred image, and thus allow dynamic calibration of the imaging sensor 120, "on demand". The acousto-optic modulator 200 can be configured to operate at a repetition rate (i.e., rate at which the acousto-optic modulator can be turned ON and OFF) on the order of kilohertz (kHz), which is sufficiently fast to perform dynamic non-uniformity correction during operation of the optical system 100 in many applications (e.g., during flight of a seeker). The efficiency of the acousto-optic modulator 200 is proportional to the acoustic power, the figure of merit of the acousto-optic material 210, and the geometry of the acousto-optic modulator (e.g., size/shape/arrangement of electrodes of the piezo-electric transducer 230), and is inversely proportional to wavelength. The controller can dynamically turn the acousto-optic modulator 200 ON and OFF, periodically, at random, or at the command of a user or other system/component.

Figure 4A:
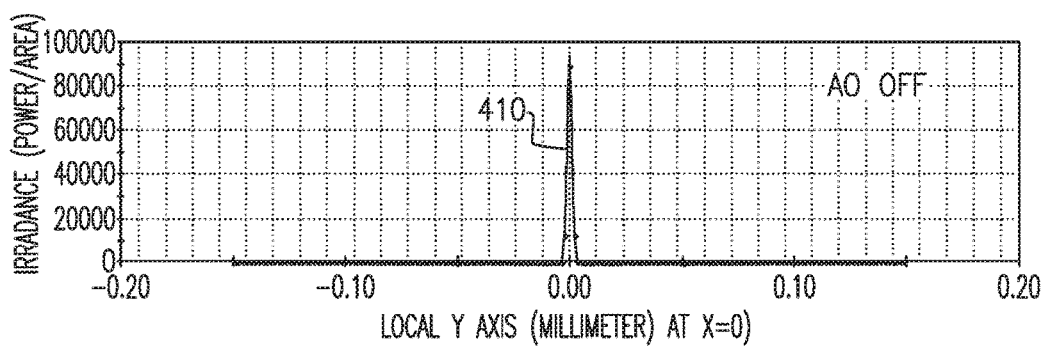
FIGS. 4A-C are graphs showing irradiance measurements at an imaging sensor for different conditions of an acousto-optic modulator in an example of the optical system of FIG. 1 according to aspects of the present invention.
Figure 4B:
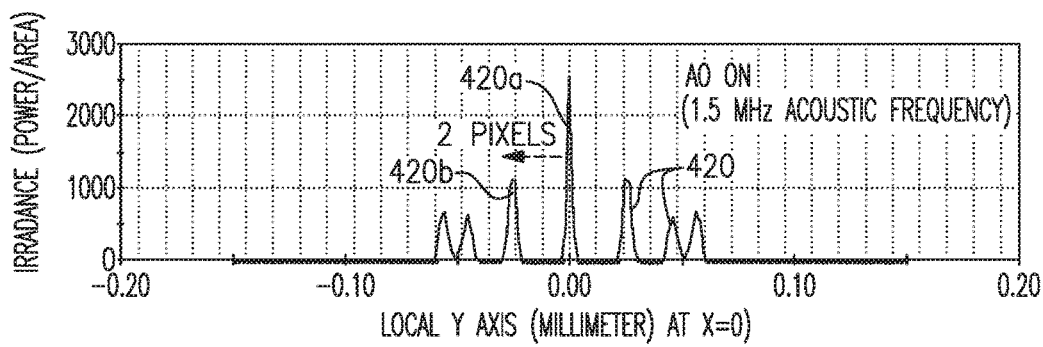
Figure 4C:
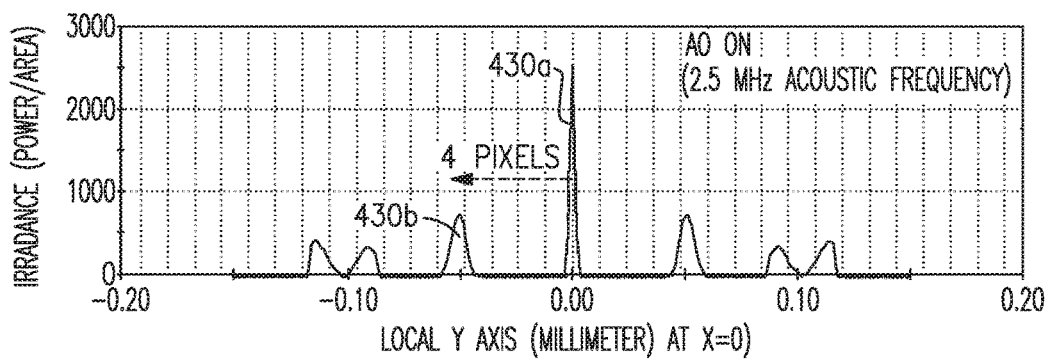

FIGS. 4A-4C are graphs showing sample theoretical predictions of a single wavelength irradiance (light intensity over area) at the imaging sensor 120 for different conditions of the acousto-optic modulator 200. The results illustrated in FIGS. 4A-C correspond to an example of the optical system 100 shown in FIG. 1 with an example of the acousto-optic modulator 200 used as the window 150, the acousto-optic material 210 being Germanium. FIG. 4A shows the irradiance measurement when the acousto-optic modulator 200 was OFF. In this case, the incident optical radiation 110 is focused on the imaging sensor 120 producing a single peak 410. FIG. 4B shows the irradiance measurement with the acousto-optic modulator 200 ON and operated at an acoustic frequency (i.e. frequency of the acoustic wave generated in the acousto-optical material 210 by the piezo-electric transducer 230) of 1.5 MHz. In this case, the optical radiation 110 is diffracted by the acousto-optic modulator 200, producing multiple peaks 420 spread over the array of detectors of the imaging sensor 120. In this example, the distance between a main peak 420a and a first "sidelobe" or "harmonic" peak 420b corresponds to two detectors in the array, or two pixels in the image. As discussed above, this diffraction and spreading of a wideband of wavelengths over the array of detectors causes the image produced to be blurry, such that it can be used as a neutral background for non-uniformity correction. FIG. 4C shows the irradiance measurement for another example in which the acousto-optic modulator 200 was ON and operated at an acoustic frequency of 2.5 MHz. In this instance, the diffraction of the optical radiation 110 again causes blurring of the image produced at the imaging sensor 120, and the distance between the main peak 430a and a first "sidelobe" or "harmonic" peak 430b corresponds to four detectors in the array, or four pixels in the image. Rapidly sweeping the diffracted orders across the imaging sensor 120 by varying the RF frequency is another way to blur the image, as discussed above.

Thus, aspects and embodiments provide a dynamic non-uniformity correction mechanism that can be easily incorporated into optical imaging systems, including infrared seekers, without requiring significant alterations to the optical configuration of the system. The acousto-optic modulator can be controlled such that the output of the imaging sensor alternates between focused and blurred images, with the blurred images being used as part of the dynamic non-uniformity correction process to help discriminate scene and target from fixed pattern noise. The acousto-optic modulator according to various embodiments can be incorporated into an existing optical component, such as the window as discussed above, and may be significantly easier to include in optical systems with tight packaging constraints and more reliable/robust than conventional mechanical non-uniformity correction mechanisms.

Figure 5:
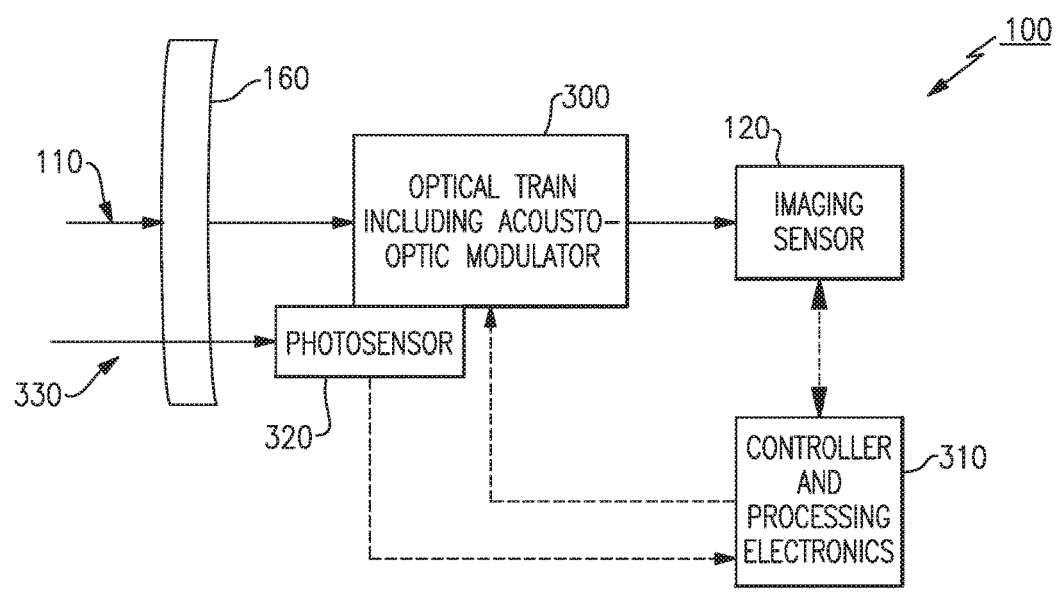
FIG. 5 is a block diagram of another example of an optical system including an acousto-optic modulator configured as a counter-countermeasure mechanism according to aspects of the present invention.

According to another embodiment, the acousto-optic modulator 200 can also (or alternatively) be configured to operate as a counter-countermeasure mechanism. FIG. 5 is a block diagram of another example of the optical system 100 including an embodiment of the acousto-optic modulator 200 and components configured to provide counter-countermeasure functionality. In this example, the optical system 100 further includes a photosensor 320 configured to detect a countermeasure beam 330. The photosensor 320 may be a photodiode, for example. The countermeasure beam 330 may be a laser beam designed to damage the imaging sensor 120 or otherwise prevent the imaging sensor 120 from obtaining useful images of a target or scene. Upon detection of the countermeasure beam 330, the photosensor 320 may provide a signal to the controller 310 to direct the controller to activate the acousto-optic modulator 200. Activation of the acousto-optic modulator 200 blurs the image formed at the imaging sensor 120, as discussed above, preventing focusing of incident radiation on the imaging sensor. Thus, the countermeasure beam 330 can be dissipated or prevented from being focused onto the imaging sensor 120 by the blurring/diffraction action of the acousto-optic modulator 200, thereby protecting the imaging sensor.

In embodiments in which the acousto-optic modulator 200 is configured to provide a counter-countermeasure mechanism, the acousto-optic modulator 200 can also function to provide non-uniformity correction as discussed above, or may be a dedicated counter-countermeasure device. The acousto-optic modulator 200 can be incorporated into the window 150 or another optical component of the optical imaging system 100, or may be a separate component included in the optical train 300. In the block diagram illustrated in FIG. 5, the photosensor 320 is shown offset from the optical train 300; however, this is for ease of illustration only. The photosensor 320 may be incorporated anywhere within the optical train 300, or with the dome 160, and may be on-axis or off-axis with respect to the optical axis of the optical imaging system 100 to collect scattered laser beam.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. An optical imaging system comprising:
   an imaging sensor configured to receive optical radiation and to produce an image of a viewed scene from the optical radiation;
   an optical train including at least one optical component configured to receive the optical radiation from the viewed scene and to focus the optical radiation to the imaging sensor; and
   an acousto-optic modulator positioned in the optical train and having an ON state and an OFF state, the acousto-optic modulator being configured in the OFF state to pass the optical radiation, and the acousto-optic modulator being configured in the ON state to diffract the optical radiation and blur the image produced by the imaging sensor from the diffracted optical radiation.

2. The optical imaging system of claim 1 wherein the acousto-optic modulator includes:
   an acousto-optic material configured to support an acoustic wave;
   a piezo-electric transducer coupled to the acousto-optic material and configured to generate the acoustic wave in the acousto-optic material in response to an RF signal applied to the piezo-electric transducer; and
   an acoustic absorber coupled to the acousto-optic material.

3. The optical imaging system of claim 2 wherein the acousto-optic material is sandwiched between the piezo-electric transducer and the acoustic absorber.

4. The optical imaging system of claim 2 wherein the acousto-optic material is Germanium.

5. The optical imaging system of claim 4 wherein the optical train includes a window, and wherein the acousto-optic modulator is integrated with the window.

6. The optical imaging system of claim 5 wherein the optical radiation is infrared radiation.

7. The optical imaging system of claim 6 wherein the optical imaging system is a seeker.

8. The optical imaging system of claim 2 wherein the acousto-optic material is one of Lithium Niobate, Gallium Phosphide, a chalcogenide glass, fused Silica, quartz, and Tellurium Oxide.

9. The optical imaging system of claim 1 further comprising a controller coupled to the acousto-optic modulator, the controller being configured to dynamically switch the acousto-optic modulator between the ON state and the OFF state.

10. The optical imaging system of claim 9 further comprising a photosensor coupled to the controller, the photosensor configured to receive a laser beam from the viewed scene and to produce a signal in response to receiving the laser beam, the controller being further configured to receive the signal from the photosensor and to switch the acousto-optic modulator into the ON state in response to receiving the signal from the photosensor.

11. The optical imaging system of claim 9 wherein the controller is configured to produce non-uniformity calibration coefficients based on outputs from the imaging sensor when the acousto-optic modulator is in the OFF state, and to adjust the image produced by the imaging sensor from the optical radiation when the acousto-optic modulator is in the OFF state to remove fixed pattern noise from the image.

12. An infrared seeker system comprising:
    an imaging sensor sensitive to infrared radiation and configured to receive the infrared radiation from a viewed scene and to produce an image from the infrared radiation;
    an optical train including at least one optical component configured to receive the infrared radiation from the viewed scene and to focus the infrared radiation to the imaging sensor; and
    an acousto-optic modulator positioned in the optical train and having an ON state and an OFF state, the acousto-optic modulator being transparent to the infrared radiation in the OFF state, and the acousto-optic modulator being configured in the ON state to diffract the infrared radiation and blur the image produced by the imaging sensor from the diffracted infrared radiation.

13. The infrared seeker system of claim 12 wherein the acousto-optic modulator includes:
    an acousto-optic material configured to support an acoustic wave;
    a piezo-electric transducer coupled to the acousto-optic material and configured to generate the acoustic wave in the acousto-optic material in response to an RF signal applied to the piezo-electric transducer; and
    an acoustic absorber coupled to the acousto-optic material.

14. The infrared seeker system of claim 13 wherein the acousto-optic material is Germanium.

15. The infrared seeker system of claim 14 wherein the at least one optical component includes at least one lens, and wherein the optical train further includes a filter and a window, the filter and the at least one lens being positioned between the window and the imaging sensor, and wherein the acousto-optic modulator is integrated with the window.

16. The infrared seeker system of claim 15 wherein the filter is configured to pass the infrared radiation in a spectral band of interest including the mid-wave infrared spectral band and the long-wave infrared spectral band and to block optical radiation outside the spectral band of interest.

17. The infrared seeker system of claim 12 further comprising a controller coupled to the acousto-optic modulator, the controller being configured to dynamically switch the acousto-optic modulator between the ON state and the OFF state.

18. The infrared seeker system of claim 17 further comprising a photosensor coupled to the controller, the photosensor configured to receive a laser beam from the viewed scene and to produce a signal in response to receiving the laser beam, the controller being further configured to receive the signal from the photosensor and to switch the acousto-optic modulator into the ON state in response to receiving the signal from the photosensor.

19. The infrared seeker system of claim 17 wherein the controller is configured to produce non-uniformity calibration coefficients based on outputs from the imaging sensor when the acousto-optic modulator is in the OFF state, and to adjust the image produced by the imaging sensor from the infrared radiation when the acousto-optic modulator is in the OFF state to remove fixed pattern noise from the image.

20. An optical imaging system with counter-countermeasure capability, the optical imaging system comprising:
- an imaging sensor configured to receive optical radiation and to produce an image of a viewed scene from the optical radiation;
- an optical train including at least one optical component configured to receive the optical radiation from the viewed scene and to focus the optical radiation to the imaging sensor;
- an acousto-optic modulator positioned in the optical train and having an ON state and an OFF state, the acousto-optic modulator being configured in the OFF state to pass the optical radiation, and the acousto-optic modulator being configured in the ON state to diffract the optical radiation and blur the image produced by the imaging sensor from the diffracted optical radiation;
- a controller coupled to the acousto-optic modulator, the controller being configured to dynamically switch the acousto-optic modulator between the ON state and the OFF state; and
- a photosensor coupled to the controller, the photosensor configured to receive a laser beam from the viewed scene and to produce a signal in response to receiving the laser beam, the controller being further configured to receive the signal from the photosensor and to switch the acousto-optic modulator into the ON state in response to receiving the signal from the photosensor.

* * * * *